US008031878B2

(12) United States Patent
Gauger, Jr. et al.

(10) Patent No.: US 8,031,878 B2
(45) Date of Patent: Oct. 4, 2011

(54) ELECTRONIC INTERFACING WITH A HEAD-MOUNTED DEVICE

(75) Inventors: Daniel M. Gauger, Jr., Cambridge, MA (US); Roman Sapiejewski, Boston, MA (US)

(73) Assignee: Bose Corporation

( * ) Notice: Subject to any disclaimer, the term of this patent is extended or adjusted under 35 U.S.C. 154(b) by 1423 days.

(21) Appl. No.: 11/191,873

(22) Filed: Jul. 28, 2005

(65) Prior Publication Data

US 2007/0025561 A1 Feb. 1, 2007

(51) Int. Cl.

| | |
|---|---|
| ***H04R 1/10*** | (2006.01) |
| ***H04R 25/00*** | (2006.01) |
| ***H04R 5/02*** | (2006.01) |
| ***A61F 11/06*** | (2006.01) |
| ***H04M 1/00*** | (2006.01) |

(52) U.S. Cl. ........... 381/74; 381/72; 381/71.6; 381/370; 381/311; 455/569.1

(58) Field of Classification Search .................... 381/74, 381/72, 71.6, 370, 311; 455/345, 297, 569.1
See application file for complete search history.

(56) References Cited

U.S. PATENT DOCUMENTS

| | | | |
|---|---|---|---|
| 5,604,813 | A | 2/1997 | Evans et al. |
| 5,765,134 | A | 6/1998 | Kehoe |
| 5,787,180 | A | 7/1998 | Hall et al. |
| 5,825,897 | A | 10/1998 | Andrea et al. |
| 5,951,141 | A | 9/1999 | Bradley |
| 5,978,689 | A | 11/1999 | Tuoriniemi et al. |
| 5,991,637 | A | 11/1999 | Mack, II et al. |
| 6,061,456 | A | 5/2000 | Andrea et al. |
| 6,108,415 | A | 8/2000 | Andrea |
| 6,415,034 | B1 * | 7/2002 | Hietanen ...................... 381/71.6 |
| 6,445,799 | B1 | 9/2002 | Taenzer et al. |
| 6,507,650 | B1 | 1/2003 | Moquin |
| 6,735,316 | B1 * | 5/2004 | Wurtz ............................. 381/74 |
| 6,873,862 | B2 | 3/2005 | Reshefsky |
| 6,975,984 | B2 | 12/2005 | MacAuslan et al. |
| 7,058,182 | B2 | 6/2006 | Kates |
| 7,110,800 | B2 | 9/2006 | Nagayasu et al. |
| 7,155,214 | B2 | 12/2006 | Struthers et al. |
| 7,181,233 | B2 | 2/2007 | Fry |

(Continued)

FOREIGN PATENT DOCUMENTS

DE 20 2006 004625 6/2006

(Continued)

OTHER PUBLICATIONS http://www.uflymike.com/index.html, pp. 1-2, Downloaded Apr. 18, 2005.

(Continued)

*Primary Examiner* — Devona Faulk

(57) ABSTRACT

Power is delivered from a power source in a head-mounted device to a separate accessory that is coupled to the head-mounted device. Power and signals are delivered on a common conductor that couples the head-mounted device to an accessory. One or both of the head-mounted device and the accessory are configured based on the signals. Power may be received at an accessory from the head-mounted device through a dedicated power conductor. Power may be delivered from a power source in a portable accessory to a head-mounted device that is coupled to the portable accessory and uses the power for circuitry in the head-mounted device that delivers audio to a user.

39 Claims, 6 Drawing Sheets

U.S. PATENT DOCUMENTS

| | | | | |
|---|---|---|---|---|
| 7,187,948 | B2 | 3/2007 | Alden | |
| 7,190,797 | B1 | 3/2007 | Johnston et al. | |
| 7,215,766 | B2 | 5/2007 | Wurtz | |
| 7,251,332 | B2 | 7/2007 | Eves et al. | |
| 7,254,420 | B1 | 8/2007 | Klein | |
| 7,292,880 | B2 | 11/2007 | Lehtonen et al. | |
| 7,346,176 | B1 | 3/2008 | Bernardi et al. | |
| 7,395,090 | B2 | 7/2008 | Alden | |
| 7,433,715 | B2 | 10/2008 | Buckley et al. | |
| 7,627,352 | B2 | 12/2009 | Gauger, Jr. et al. | |
| 7,720,232 | B2 | 5/2010 | Oxford | |
| 2001/0050991 | A1 | 12/2001 | Eves | |
| 2001/0050993 | A1 | 12/2001 | Douglas | |
| 2001/0053228 | A1 | 12/2001 | Jones | |
| 2002/0003889 | A1 * | 1/2002 | Fischer | 381/370 |
| 2002/0102005 | A1 | 8/2002 | Lin | |
| 2004/0136522 | A1 | 7/2004 | Wurtz | |
| 2004/0198436 | A1 | 10/2004 | Alden | |
| 2004/0204185 | A1 | 10/2004 | Snyder et al. | |
| 2005/0004796 | A1 | 1/2005 | Trump et al. | |
| 2005/0064915 | A1 | 3/2005 | Lair | |
| 2005/0090295 | A1 | 4/2005 | Ali et al. | |
| 2005/0130697 | A1 | 6/2005 | Dyer | |
| 2005/0146227 | A1 | 7/2005 | Jackson et al. | |
| 2005/0177365 | A1 | 8/2005 | Ikeda | |
| 2005/0181826 | A1 | 8/2005 | Yueh | |
| 2005/0232448 | A1 | 10/2005 | Kung | |
| 2005/0239434 | A1 | 10/2005 | Marlowe | |
| 2006/0013410 | A1 | 1/2006 | Wurtz | |
| 2006/0046656 | A1 | 3/2006 | Yang | |
| 2006/0046778 | A1 | 3/2006 | Hembree | |
| 2006/0134959 | A1 | 6/2006 | Ellenbogen | |
| 2006/0166705 | A1 | 7/2006 | Seshadri et al. | |
| 2006/0193479 | A1 | 8/2006 | Harvey et al. | |
| 2007/0015486 | A1 | 1/2007 | Marlowe | |
| 2007/0025561 | A1 | 2/2007 | Gauger et al. | |
| 2007/0036384 | A1 | 2/2007 | Struthers et al. | |
| 2007/0041582 | A1 | 2/2007 | Lam | |
| 2007/0082612 | A1 | 4/2007 | Valve et al. | |
| 2007/0127747 | A1 | 6/2007 | Doyle | |
| 2007/0184881 | A1 | 8/2007 | Wahl et al. | |
| 2007/0225035 | A1 | 9/2007 | Gauger et al. | |
| 2007/0226384 | A1 | 9/2007 | Robbin et al. | |
| 2007/0239849 | A1 | 10/2007 | Robbin et al. | |
| 2007/0247794 | A1 | 10/2007 | Jaffe et al. | |
| 2007/0291953 | A1 | 12/2007 | Ngia et al. | |
| 2008/0032752 | A1 | 2/2008 | Tamura | |
| 2008/0101638 | A1 | 5/2008 | Ziller | |
| 2008/0167092 | A1 | 7/2008 | Ueda et al. | |
| 2008/0187160 | A1 | 8/2008 | Kim | |
| 2008/0201138 | A1 | 8/2008 | Visser et al. | |

FOREIGN PATENT DOCUMENTS

| | | | |
|---|---|---|---|
| EP | 0583900 | | 2/1994 |
| EP | 1091543 | | 4/2001 |
| EP | 1608202 | | 12/2005 |
| GB | 234308 | | 5/1925 |
| GB | 2 272 129 | A | 5/1994 |
| GB | 2343080 | | 4/2000 |
| JP | 2000224683 | A | 8/2000 |
| JP | 2001016679 | A | 1/2001 |
| JP | 2001100794 | A | 4/2001 |
| JP | 2001103355 | A | 4/2001 |
| WO | WO 00/10362 | | 2/2000 |
| WO | WO 00/38044 | | 6/2000 |
| WO | 0203746 | | 1/2002 |
| WO | WO 02/01910 | | 1/2002 |
| WO | WO 0201910 | A2 * | 1/2002 |
| WO | WO 2004/080123 | | 9/2004 |
| WO | 2005029825 | | 3/2005 |
| WO | 2006129205 | | 12/2006 |
| WO | WO 2006/130115 | | 12/2006 |
| WO | WO 2007/031703 | | 3/2007 |
| WO | WO 2007/049075 | | 3/2007 |

OTHER PUBLICATIONS

The Bose Avidation Headset X Owner's Guide, Version AM270261_00V.pdf, Mav 16 2003.

The Bose QuietComfort Acoustic Noise Cancelling Headphones Guide, Version AM257565_00_V.pdf, May 13, 2003.

Combat Vehicle Crewman Headset Brochure Bose Corporation 2000.

Combat Vhicle Crewman Headset Parts List Bose Corporation 1998.

International Search Report and Written Opinion in Application No. PCT/US2008/050216, dated Sep. 4, 2008.

Tekkeon, myTalker Compatibility, http://www.tekkeon.com/site/products-mytalker.compat.php, downloaded Jan. 24, 2006. Site Copyright 2004, 2005, Publication date unknown. <http://www.tekkeon.com/site/products-mytalker-ompat.php>.

Tekkeon, myTalker Tech Specs, http://www.tekkeon.com/site/products-mytalker-specs.php, downloaded Jan. 24, 2006, Site Copyright 2004, 2005, Publication date unknown. <http://www.tekkeon.com/site/products-mytalker-specs.php>.

Tekkeon, myTalker Features, http:www.tekkeon.com/site/products-mytalker-features.php, downloaded Jan. 24, 2006, Site Copyright 2004, 2005, Publication date unknown.

Tekkeon, myTalker Bluetooth Gateway for iPod and MP3 Players Data Sheet, Copyright 2006, Site Copyright 2004, 2005, Publication date unknown.

Hardware Zone, Tekkeon Enables Mobile Phone Calls Using iPod/MP3 Headphones, San Francisco, MacWorld, Jan. 10, 2006. http://www.hardwarezone.com/news/view.php?id3523&cid=2&src=rss, downloaded Jan. 24, 2006.

TreoCentral.com SkullCandy headset? pp. 1-3, http://discuss.treocentral.com/archive/index.php/t-33954.html, downloaded Nov. 3, 2005, Publication date unknown. <http://discuss.treocentral.com/archive/index.php/t-33954.html>.

Amazon.com: Electronics: Skullcandy SCE-3B Skullcandy Earbud with 3-Barrel Universal Cell Phone Connector, p. 1 of 1, http//www.amazon.com/gp/product/B00009WE3O/sr=1-18/qid=1131032711/ref=sr_1_18/102-71..., downloaded Nov. 3, 2005, Publication date unknown.

Amazon.com: Electronics: Skullcandy SCE-3B Skullcandy Backphones with 3-Barrel Universal Cell Phone Connector, p. 1 of 2, http//www.amazon.com/gp/product/B00009WE3M/102-7181297-1030518?v=glance&n=172282..., downloaded Nov. 3, 2005, Publication date unknown.

Bluetake i-Phone BT420EX Bluetooth Hi-Fi Sports Headphone Kit; Bluetake Bringing Enhanced enjoyment ; from website: www.bluetake.com/products/BT420EX/BT420EXsubS.htm (Nov. 3, 2005).

Bluetake Technology BT420, Bluetooth, Hi-Fi Sports Headphone, Copyright 2004. www.bluetake.com., Publication date unknown. <http://www.bluetake.com/>.

BlueTake BT420ex Bluetooth Stereo Headset, pp. 1 of 2, http//www.behandsfree.com/ProductInfo.aspx?productid=WHEAD1014, downloaded Nov. 3, 2005, Publication date unknown.

Anonymous, "Combining telephone capability with portable music devices", vol. 43, No. 665, Research Disclosure, Mason Publications (Mar. 2001).

"Bluetooth Wireless Stereo Solutions, User Manual (GBMA201, GBMH201, GBMHKIT)," IOGEAR, Copyright 2005 (retrieved on May 26, 2008), retrieved from the Internet: <URL:http://www.iogear.com/support/dm/manual/GBMH201#display>.

"Blueye Cyclops Bluetooth Stereo Headphone," Philippines Hardware Zone, Jan. 29, 2006 (retrieved on May 26, 2008), retrieved from the Internet: <URL:http://ph.hardwarezone.com/news/view.php?cid=8&id=3526>.

Invitation to Pay Additional Fees dated Jun. 6, 2008 from International Application PCT/US2008/050216.

Amazon.com: Electronics: Skullcandy SCE-N4 Skullcandy Earbud For Nokia; 4-Barrel 2.5 MM Pin . . . p. 1 of 1, http//www.amazon.com/gp/product/tech-data/B00009WE3P/ref=dp_nav_0/102*7181297-103051..., downloaded Nov. 3, 2005, Publication date unknown.

Skullcandy, Portable Link User's Guide, pp. 1-2, http://www.skullcandy.com/manuals/LinkUserGuide.pdf, downloaded Nov. 11, 2005.
http:/lwww.uflymike.com/index.htm, pp. 1-2, Downloaded Apr. 18, 2005. <http://www.uflymike.com/index.htm>.
The Bose Aviation Headset X Owner's Guide, Version AM270261_OOV.pdf, May 16, 2003.
The Bose QuietComfort Acoustic Noise Cancelling Headphones Guide, Version AM257565 00 V.odf, May 13, 2003.
Combat Vehicle Crewman Headset Parts List Bose Corporation 1998.
Skullcandy SCE-3B Skullcandy Earbud With 3-Barrel Universal Cellphone Connector; from website: Amazon.com: Electronics: Skullcandy SCE-3B Skullcandy Earbud; Nov. 3, 2005.
International Preliminary Report on Patentability dated Mar. 19, 2009 for Appl. No. PCT/US08/050216.
theBoom Quiet. http://www.theboom.com/ProductDetails.asp?ProductCode=571&Show=TechSpects downloaded Jan. 3, 2007.
Creative Worldwide Headset CB2455. http://www.creative.com/products/product.asp?category=437&subcategory=442&product downloaded Jan. 3, 2006.
Plantronics Pulsar 590A Bluetooth® Headset. http://www.headsetgenie.comlproduct info.php?cPath=8&productsid=318 downloaded Jan. 3, 2007.
Skullcandy SCB-3B Skullcandy Backphones With 3-Barrel Universal Cellphone Connector; from website: Amazon.com: Electronics: Skullcandy SCB-3B Skullcandy Backphones; Nov. 3, 2005 (2 pages).
Globeandmail.com; Skullcandy Link by Jack Kapica, from website: www.globetechnology.com/servlet/story/RTGAM.20031021.gtskullrevoct21; Nov. 3, 2005 (2 pages).
Certificate of Patent for Utility Model dated Mar. 3, 2010 for CN Patent No. ZL200890000013.7.
JP Office Action dated Jan. 26, 2010 for JP Appl. No. JPO2009-600045_000424.
JP Office Action dated Jan. 26, 2010 for JP Appl. No. JPO2009-600045_000425.
International Search Report and Written Opinion dated Aug. 16, 2007 for Appl. PCT/US07/064913.
International Preliminary Report on Patentability dated Mar. 10, 2008 for Appl. No. PCT/US07/064913.
AU Office Action dated Jun. 1, 2010 for AU Appln. No. 2008205121.
International Preliminary Report on Patentability dated May 12, 2007 for Appl. No. PCT/US06/028605.
International Search Report and Written Opinion dated Dec. 6, 2006 for Appl. No. PCT/US06/028605.
CN Notice of Grant dated Oct. 23, 2009 for CN Appl. No. 200890000013.7.

* cited by examiner

ELECTRONIC INTERFACING WITH A HEAD-MOUNTED DEVICE

BACKGROUND

This description relates to electronic interfacing with a head-mounted device.

Audio signals, for example, are typically carried to a headphone through a multiple-conductor cable ending in a plug that fits into a jack of a player or radio. When a microphone is added to the headphone to form a headset, the microphone signal also may be carried through the same cable to a device that uses the microphone signal, such as a telephone set or a recorder. In aviation headsets, the cable may be detachable at a jack on the headset to permit changes in the use of the headset.

The connecting cable may also be disconnected from typical noise reduction headphones when the user is using only the noise reduction feature and is not using audio from a player or radio. The circuits that are part of noise reduction headphones may be powered by batteries mounted in the headphones.

In some military communication headsets, a detachable microphone plug may both carry the microphone signal to an intercom circuit and microphone power.

Headsets that can be plugged into cell phones for hands-free use commonly use electret microphones that receive bias voltage from the cell phone's power source.

Portable music players may provide power to run electronics in peripheral devices such as transmitters to an FM radio in, for example, an automobile.

In the Universal Serial Port (USB) standard, power may be provided by a USB host or hub to a USB peripheral through a USB connector. The host and peripheral may exchange messages (using the USB standard's handshaking and power management features) regarding one another's identity and operational parameters. The messages may include how much power the peripheral will use in different operational states or the amount of memory available in the peripheral. USB headsets may be configured as peripherals in interaction with other devices.

SUMMARY

In general, in one aspect, power is delivered from a power source in a head-mounted device to a separate accessory that is coupled to the head-mounted device.

In general, in another aspect, power and signals are delivered on a common conductor that couples a head-mounted device to an accessory.

In general, in another aspect, signals are passed back and forth between a head-mounted device and an accessory that is coupled by conductors to the head-mounted device, and one or both of the head-mounted device and the accessory are configured based on the signals.

In general, in another aspect, power is received at an accessory from a head-mounted device through a power conductor, for example, a dedicated power conductor.

In general, in another aspect, an audio device to be mounted on a head comprises a transducer to deliver sound to an ear and a power source, and a conductor delivers power from the power source to an accessory coupled to the audio device.

In general, in another aspect, an audio device mounted on a head includes a transducer to deliver sound to an ear, a power source, and a signaling device, and a common conductor carries power from the audio device to an accessory and signals between the audio device and the accessory.

In general, in another aspect, an audio device to be mounted on a head includes a transducer to deliver sound to an ear, a signaling device to communicate with an accessory that is connected to the audio device, and a wired channel to carry configuration signals back and forth between the head-mounted audio device and the accessory.

In general, in another aspect, an audio device to be mounted on a head includes a transducer to deliver sound to an ear, a power source, and a dedicated power conductor to deliver power from the power source to an accessory coupled to the audio device, and a wired channel carries configuration signals back and forth between the head-mounted audio device and an accessory that is connected to the audio device.

In general, in another aspect, an accessory to be coupled to a head-mounted device has a conductor to connect to a dedicated power conductor of the device to receive power for the accessory.

In general, in another aspect, an accessory having a signaling device conducts wired communication of configuration signals with a head-mounted device.

In general, in another aspect, an accessory having a common conductor carries power and signals between the accessory and a head-mounted device.

In general, in another aspect, an accessory has a device that uses power and a conductor receives power for the device from a head-mounted device.

In general, in another aspect, power is delivered from a power source in a portable accessory to a head-mounted device that is coupled to the portable accessory and uses power for circuitry in the head-mounted device that delivers audio to a user.

Implementations may include one or more of the following features. The head-mounted device comprises at least one of a headphone and a headset. The head-mounted device comprises an audio device. The head-mounted device includes at least one of active noise reduction circuitry, amplification circuitry, or audio processing circuitry. The accessory comprises at least one of a music player, a wireless receiver, a wireless transceiver, or a radio. The device and the accessory are coupled using a detachable cable that includes the conductor. The signals comprise at least one of command, control, or management signals. The power is delivered from a source of power in the head-mounted device. The source of power comprises a battery. The accessory is peripheral to the head-mounted device. The power conductor is dedicated to delivering power.

Other advantages and features will become apparent from the following description and the claims.

DESCRIPTION

Figure 1:
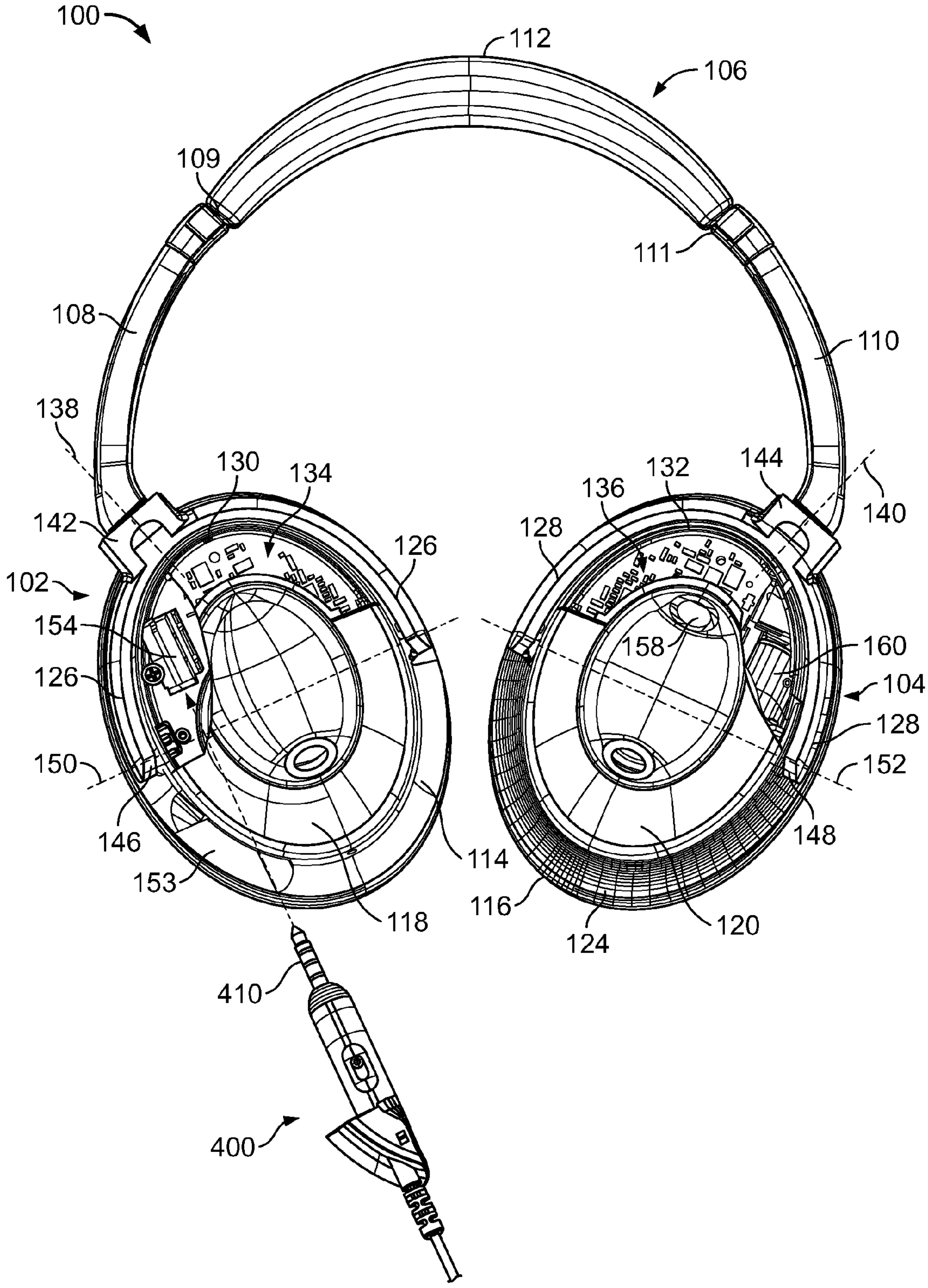
FIG. 1 is a front view of a headphone partially cutaway.

As shown in the specific example of FIG. 1, an audio headphone 100 is served by a detachable accessory cable 400 that provides an interface between the headphone and an accessory (not shown), for example, a stereo or MP3 player, a microphone for voice sensing, an aviation or helicopter interface cable, a cable connection to a USB host, or a module 162 (described below) that connects directly to the headphone 100. The headphone 100 is an example of a head-mounted device. A headset (which includes a microphone) is another example. The phrase head-mounted device is meant to include every possible sort of electronic device that is mounted on the head or any part of the head (for example an ear or a nose or the hair) for use by a wearer.

The detachable accessory cable 400 may allow for a functional reconfiguration of the headphone 100 for various platforms. For example, an internal battery 160 that is used to power electronics 134 and 136 (e.g., Active Noise Reduction, ANR) in the headphone 100 may also be used to power electronics in the accessory cable 400 or in the accessory to which the cable is connected.

The connection between the detachable accessory cable 400 and the headphone 100 may be through a 3.5 mm, 0.25 in, or other diameter jack plug or telephone plug 410. Other types of connectors may be used, for example connectors similar to the parallel-contact ones commonly found on some cell phones. Power may be supplied from the headphone 100 to the accessory cable 400 by one of the four metal contacts of the plug 410. The power provided by the headphone 100 to the electronics in the accessory cable 400 may be voltage regulated power, current regulated power, raw battery power, DC, AC, fuel cell, or solar cell, or any other power source.

In addition to providing power, the detachable accessory cable 400 may serve as a wired channel to carry control or management signals between the headphone 100 and the accessory, for example, for use in handshaking and configuration (described below).

The headphone 100 includes a left earcup 102 and a right earcup 104 connected to a headband 106 that includes a left adjustment sleeve 108 fixed to a center span 112 by a connector 109 and a right adjustment sleeve 110 connected to the center span 112 by a connector 111. In some examples, the headband 106 may be comprised of other numbers and configurations of elements. The left adjustment sleeve 108 and the right adjustment sleeve allow the wearer to adjust the position of the left earcup 102 and the right earcup 104 relative to the center span 112 to accommodate size requirements and comfort preferences of different wearers.

Shown as a partial cutaway in FIG. 1, the left earcup 102 includes an earcup housing 114, an earcup cover 118, an earcup audio seal (not shown in FIG. 1), and an earcup angular adjustment mount 126.

Similarly, the right earcup 104 (also shown as a partial cutaway in FIG. 1) includes an earcup housing 116, an earcup cover 120, an earcup audio seal 124, and an earcup angular adjustment mount 128.

The earcup cover 118 is connected to the earcup housing 114 to define a left earcup chamber 130. The earcup cover 120 is connected to the earcup housing 116 to form a right earcup chamber 132. The left and right earcup chambers 130 and 132 contain left and right electronics 134 and 136, respectively. In the example of FIG. 1, the left and right electronics 134 and 136 provide and control headphone 100 functions that may include ANR, headphone power supply, and accessory power management (described below).

The left earcup 102 is rotatably connected to the left adjustment sleeve 108 by the earcup adjustment mount 126. The earcup adjustment mount 126 may comprise one or more rotational connectors 142 and 146. The earcup adjustment mount 126, as shown in this example, may comprise a rotational pin 146 and a rotational connector 142. The rotational pin 146 enables the left earcup 102 to be rotatably adjusted about an axis 150. The rotational connector 142 enables the left earcup 102 to be rotatably adjusted about a longitudinal axis 138.

Similarly, the right earcup 104 is rotatably connected to the right adjustment sleeve110 by the earcup adjustment mount 128. The earcup adjustment mount 128 may comprise one or more rotational connectors 144 and 148. The earcup adjustment mount 128, as shown in this example, may comprise a rotational pin 148 and a rotational connector 144. The rotational pin 148 enables the right earcup 104 to be rotatably adjusted about an axis 152. The rotational connector 144 enables the right earpiece 104 to be rotatably adjusted about a longitudinal axis 140.

In FIG. 1, the audio headphone 100 is shown in a stowage position. The left earcup 102 and the right earcup 104 have been rotated about longitudinal axes 138 and 140, respectively. In the stowage position, the earcup cover 118 of the left earcup 102 and the earcup cover 120 of the right earcup 104 lie in a common plane.

The cutaway of the earcup cover 118 reveals an opening to an accessory insertion channel 153 for the accessory plug 410. The cutaway of the earcup cover 118 also reveals the electronics 134 that may be contained within the left earcup chamber 130. The electronics 134 may include a jack 154 that mates with the plug 410 of the accessory cable 400 to permit electronic interfacing with the accessory power management circuit, left earcup speaker, and the left earcup ANR electronics. Similarly, the cutaway of the earcup cover 120 reveals the electronics 136 which may be contained within the right earcup chamber 132. The electronics 136 includes an ANR enable switch 158, the battery 160 for the headphone power supply, the headphone power supply circuit, the right earcup speaker, and the right earcup ANR electronics.

Figure 2:
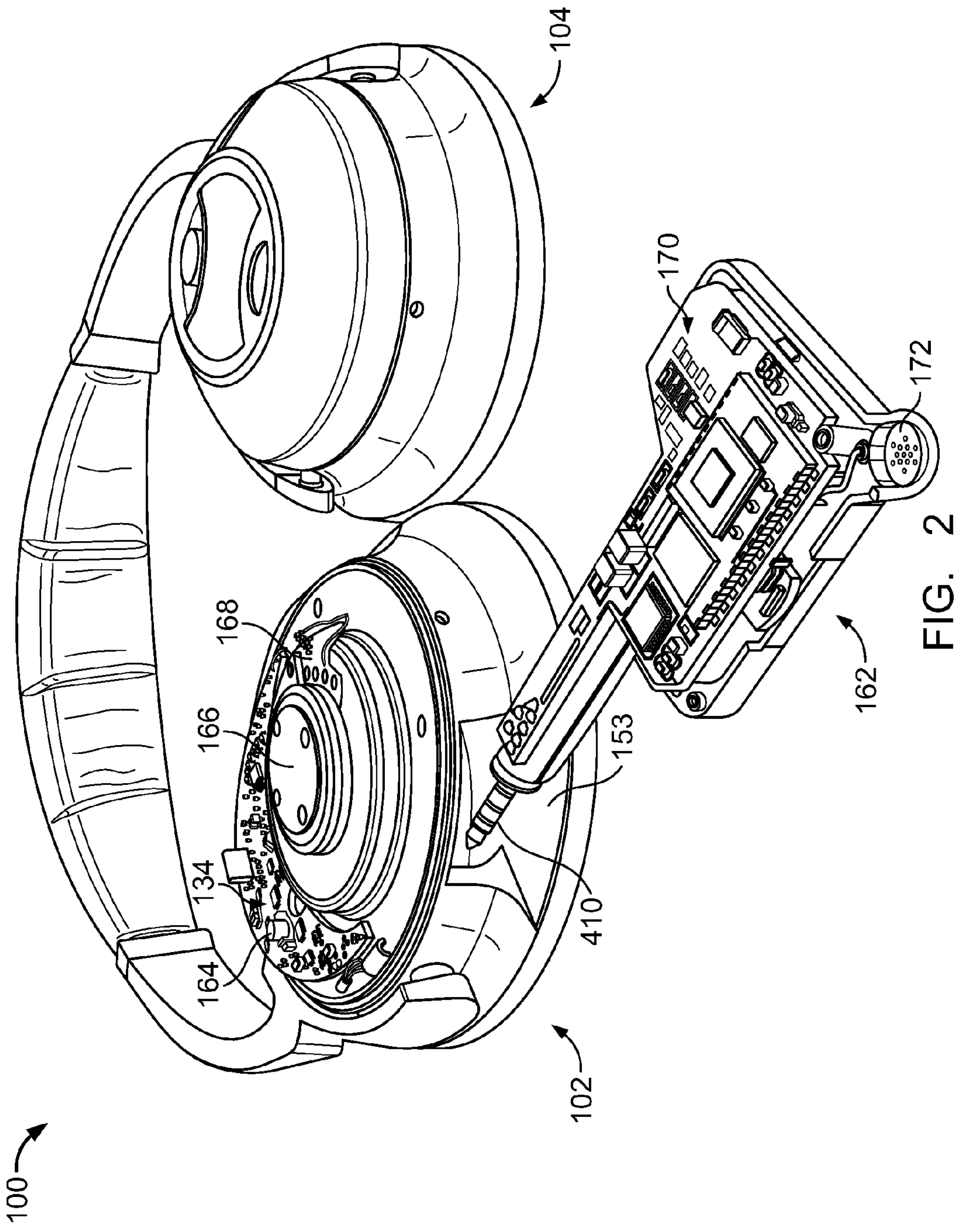
FIG. 2 is a perspective view of an accessory module and a headphone.

Referring to FIG. 2, an example accessory module 162 connects directly through the accessory insertion channel 153 using an accessory plug 410 mounted on the accessory module 162, rather than using a cable. The earcup cover 118 of the left earcup 102 has been removed to reveal the electronics 134 mounted within the left earcup chamber 130. The electronics 134 revealed by the removal of the earcup cover 118 may include the accessory power management electronics 164, left earcup speaker 166, and the left earcup ANR electronics 168.

The example accessory module 162 includes electronics 170 that provide the wearer with a hands-free wireless (e.g., Bluetooth) connection to a cell phone (not shown). The accessory module 162 also may include a microphone 172 that may pick up the sound of a wearer's voice. The accessory module 162 and the microphone 172 receive power from the headphone battery 160. In some implementations, the accessory module may include electronics 170 that, for example, provide the wearer with a wireless connection to a stereo or MP3 player audio source, an aviation or helicopter interface, a USB host, or the like.

The detachable module 162 may allow for a functional reconfiguration of the headphone 100 for use on a variety of platforms. For example, the headphone 100 may contain an internal battery (not shown) to power the ANR electronics 168 in the headphone 100. The internal battery may be used to power electronics in the accessory module 162 that may interface with the headphone 100. The power may be supplied from the headphone 100 to the accessory module 162 by one of the contacts on the plug 410. The power provided by the headphone battery 160 to the electronics 170 in the accessory module 162 may be raw battery power, power that is voltage or current regulated by the accessory power management electronics 164 (discussed in FIGS. 3 and 4), or any other power source.

Some implementations may include signaling capabilities between the headphone 100 and the accessory module 162.

The signaling capabilities may be used for a wide variety of purposes and functions, including handshaking, power supply configuration, or signal configuration between the headphone 100 and the accessory module 162.

Figure 3:
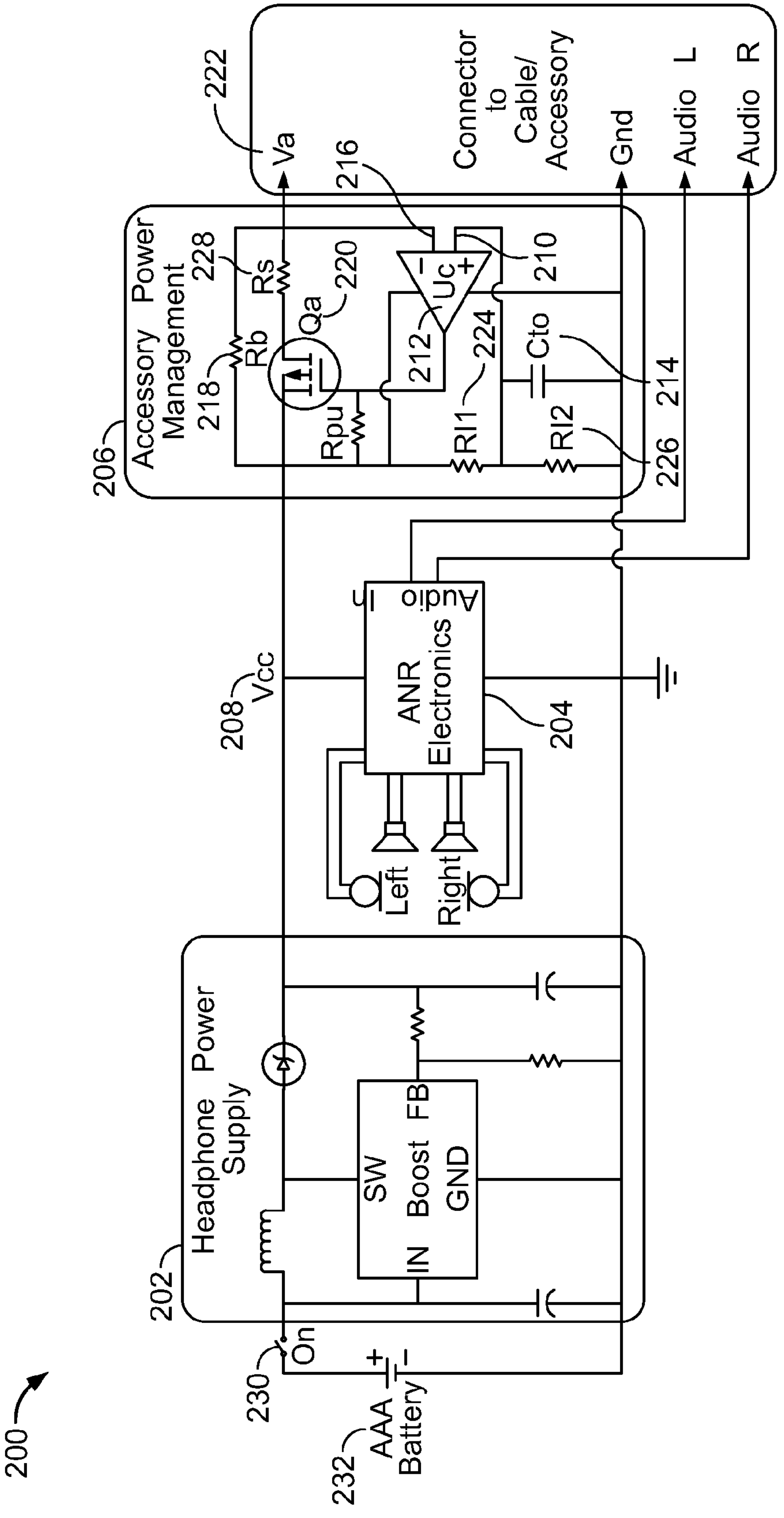
FIGS. 3 and 4 are schematic diagrams.

As shown in FIG. 3, an example circuit 200 that may be mounted in the headphone includes a boost converter 202 to power the ANR headphone electronics 204 and an accessory power management circuit 206. Circuit 200 is a portion of headphone right earcup electronics 136 or alternatively a part of left earcup electronics 134 or in some other location in the headphone. The accessory power management circuit 206 may turn off the power supply to the accessory (e.g., 400 and 162) if the current drawn by the accessory (e.g., 400 and 162) exceeds a maximum predetermined supply threshold.

The operation of the accessory power management circuit 206 is as follows. When the headphone 100 is first turned on using switch 230, Vcc 208 increases to a nominal value of 2.8 Vdc because of the action of boost circuit 202. The +input pin 210 of comparator Uc 212 is held to a low voltage as capacitor Cto 214 charges. The −input pin 216 of comparator Uc 212 is held to a higher voltage through Rb 218 so the comparator Uc 212 will initially pull its output low, turning on MOSFET Qa 220. MOSFET Qa 220 provides power Va 222 to the accessory (e.g., 400 and 162). The time constant which is approximately R11*Cto (items 224 and 214), since R12 is normally much greater than R11 may be chosen so that Qa 220 may be held on by +input pin 210 of comparator Uc 212 being held to a low enough voltage for the duration of any initially high turn-on current spikes drawn by the accessory (e.g., 400 and 162).

Subsequently, if the current drawn from Va 222 by the accessory (e.g., 400 and 162) exceeds a predetermined value such that the voltage drop across the sense resistor Rs 228 exceeds the drop across R11 224 in the R11/R12 224/226 divider, then comparator Uc 212 output will go to logic high level, Qa 220 will turn off, and Va 222 will fall to essentially zero, latching the accessory (e.g., 400 and 162) power off. The wearer would need to turn the headphone 100 power off and back on using the switch 230 in order to once again provide power to the accessory (e.g., 400 and 162). This example is just one possible implementation.

Some implementations of the accessory power management circuit 206 may include replacing the accessory power management circuit 206, as shown in FIG. 3, with no power management. In such examples, Va 222 may be directly connected to Vcc 208 and current limiting in the power supply 202 may be desirable. Possible current limiting implementations may include a resistor, a circuit, or a device that clamps the current to a maximum value (e.g., a Junction Field Effect Transistor (JFET) connected to limit current to its saturation value Idss). Another example may include a voltage regulator (either switching or linear) to regulate Vcc 208 to the Va 222 required by the cable or module accessories 400 and 162. In some implementations for power management, the headphone power supply 202 may also be a raw voltage or a higher voltage (e.g., lithium polymer) from a battery 232 and a buck converter to create the Vcc 208 that the headphone 100 requires.

Figure 4:
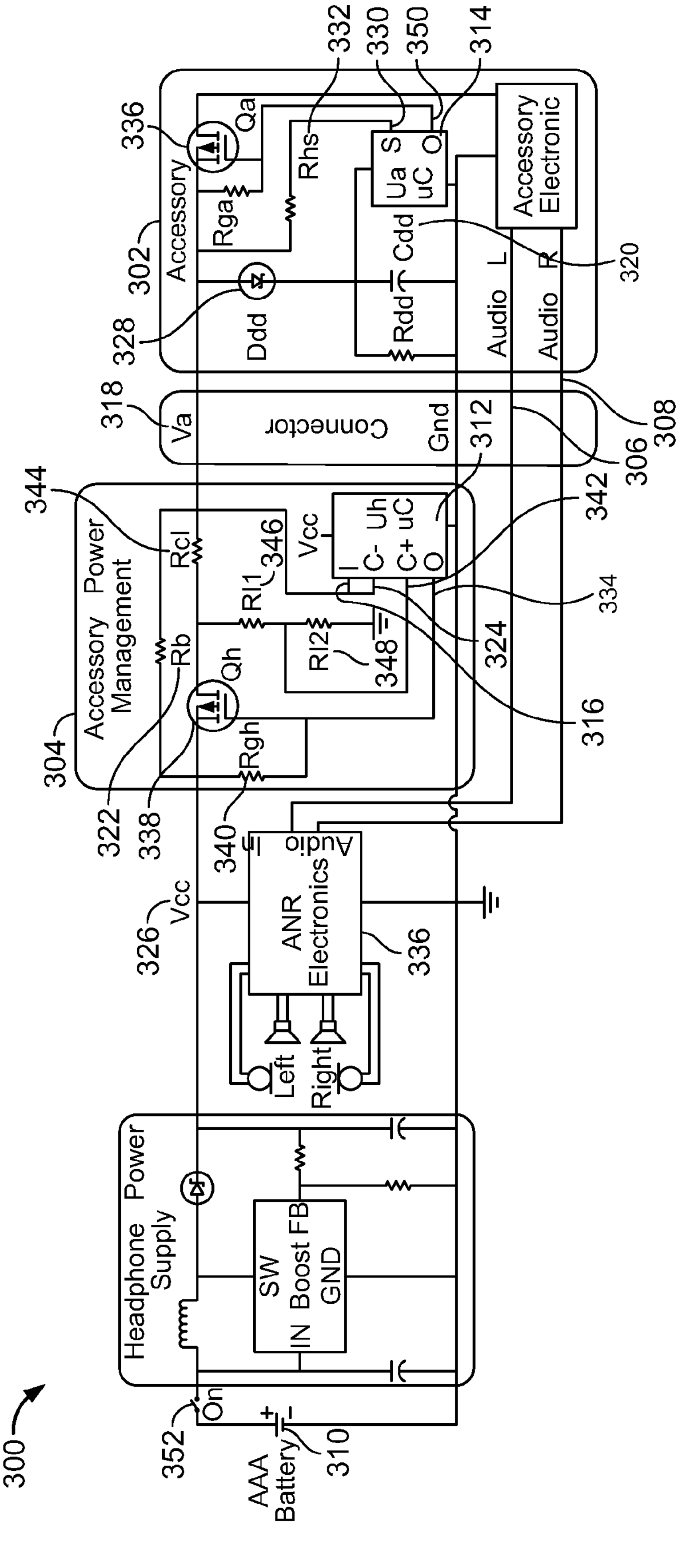

Referring to FIG. 4, in some examples of the circuit 300 power management and signaling electronics 304 enable signaling between the headphone 100 and the powered accessory device 302 on a conductor shared with voltage Va 318 provided to the accessory 302. For example, the circuit 300 may enable electrical handshaking and configuration signaling between the headphone 100 and the powered accessory device 302. The electronics 304 could replace the power management circuitry 206 with circuitry to implement an exemplary handshaking and configuration protocol between the headphone 100 and accessory 302 while also managing power flow. The protocol may allow the accessory 302 to pass a binary or integer value N to the headphone 100 upon power-up. This value N may be used to identify whether the accessory 302 is compatible for use with that headphone 100 or to configure the headphone 100 in some fashion.

Examples of headphone 100 configurations may include presenting a 32 ohm load through a cable connection accessory cable 400 to a typical audio source (e.g., home stereo) to emulate traditional passive consumer headphones. Another example may include switching the left and right inputs 306 and 308 of the headphone 100 to a high impedance state when connected to a wireless accessory module 162 to minimize power consumption and draw on the battery 310.

In such examples, the circuit includes two microcontrollers 312 and 314. The microcontroller Uh 312 is part of the headphone electronics 134. The microcontroller Ua 314 is part of the accessory 302 electronics. The two microcontrollers 312 and 314 may be Microchip Technology Inc. PIC-10F integrated circuits. Some implementations may use more sophisticated controllers that may already be present in the electronics of either the headphone 100 or the accessory 302 to accomplish similar or additional functions. The microcontrollers 312 and 314 may have code that may be flashed into memory to allow the implementation of the following handshaking and configuration protocol: while the headphone 100 power switch 352 is turned to the on position, the microcontroller Uh 312 checks input I 316 periodically (typically every 10 milliseconds) to see if the voltage Va 318 is low. This is to detect the mating (or presence upon power up) of an accessory 302.

When an accessory 302 is mated, the capacitor Cdd 320 (typically 10 uF) charges through the resistor Rb 322 (typically 2 Kohm) until the voltage is high enough for the microcontroller Ua 314 to be enabled. The microcontroller Ua 314 then waits several time constants Rb*Cdd 322 and 320, allowing Ua's 314 supply input feed by the voltage of Cdd to approach Vcc 326 less the drop across the Schottky diode Ddd 328, before pulling the output S 330 to a logic low level. S 330 is held at a logic low level long enough (typically 15 milliseconds) for the microcontroller Uh 312 to detect the presence of accessory 302. Rhs 332 is of a small enough value to ensure that Va 318 is pulled below a predetermined threshold of microcontroller Uh 312 input I 316. At wake-up, and during all handshaking, microcontroller Ua 314 pin O 350 is held high to keep MOSFET Qa 336 off, preventing the accessory 302 from operating. After having held output S 330 to a logic low level for 15 milliseconds (typically), microcontroller Ua 314 then releases S 330 to allow Cdd 320 to recharge to ensure sufficient voltage to keep powering microcontroller Ua 314 (typically 40 milliseconds). When microcontroller Uh 312 detects that input I 316 (voltage Va 318) has returned to a logic high state it begins checking pin I 316 much more often (i.e., every 100 microseconds). This begins the accessory handshake sequence. After Cdd 320 recharges, the microcontroller Ua 314 pulls S 330 to a logic low level for 150 microseconds (typically), ensuring that the microcontroller Uh 312 detects that the input I 316 (voltage Va 318) is at a logic low level. When the microcontroller Uh 312 detects Va 318 is at a logic low level it zeros a handshake register. The microcontroller Uh 312 continues checking the state of input I 316 every 100 microseconds. Every fourth check (i.e., every 400 microseconds) the value in the handshake register is incremented by one.

After the first 150 microsecond (typically) strobe of pin S 330, the microcontroller Ua 314 waits some multiple N of 400 microseconds to strobe output S 330 low for another 150 microsecond (typically) interval. The value of N is the information the accessory 302 wishes to pass to the headphone 100 during the handshaking process. When the microcontroller Uh 312 detects that the microcontroller Ua 314 has pulled Va low a second time, the 100-microsecond checking cycle and the handshaking process is complete with the handshake register now containing the value N passed from the accessory 302. In the circuit 300, as shown, N is compared against a stored list in the headphone 100 to determine if the accessory is compatible. If the accessory is compatible, the microcontroller Uh 312 pulls output O 334 low turning on the MOSFET Qh 338 to provide power to the accessory 302. The gate of Qh 338 has been held to a logic high level by a pull-up resistor Rgh 340. The output O 334 could also be passed to the ANR electronics 336 to accomplish some other configuration, such as the impedance matching mentioned earlier.

Meanwhile, after the second handshake-completing strobe of pin S 330, the microcontroller Ua 314 waits for the microcontroller Uh 312 to complete the handshake process and configure the headphone 100. It then pulls the output O 350 low, turning on the MOSFET Qa 336, providing power to the accessory 302 electronics. After the microcontroller Uh 314 turns on Qh 338, the microcontroller Uh 312 then begins monitoring comparator inputs C+ 342 and C− 324. If C− 324 falls below the value at C+ 342, the accessory 302 has drawn current exceeding the designed limit and transistor Qh 338 is turned off by microcontroller Uh 312 output O 334. The current limit is determined by current sense resistor Rcl 344 (typically 1 ohm) and limit setting resistors R11 346 and R12 348.

Figure 5:
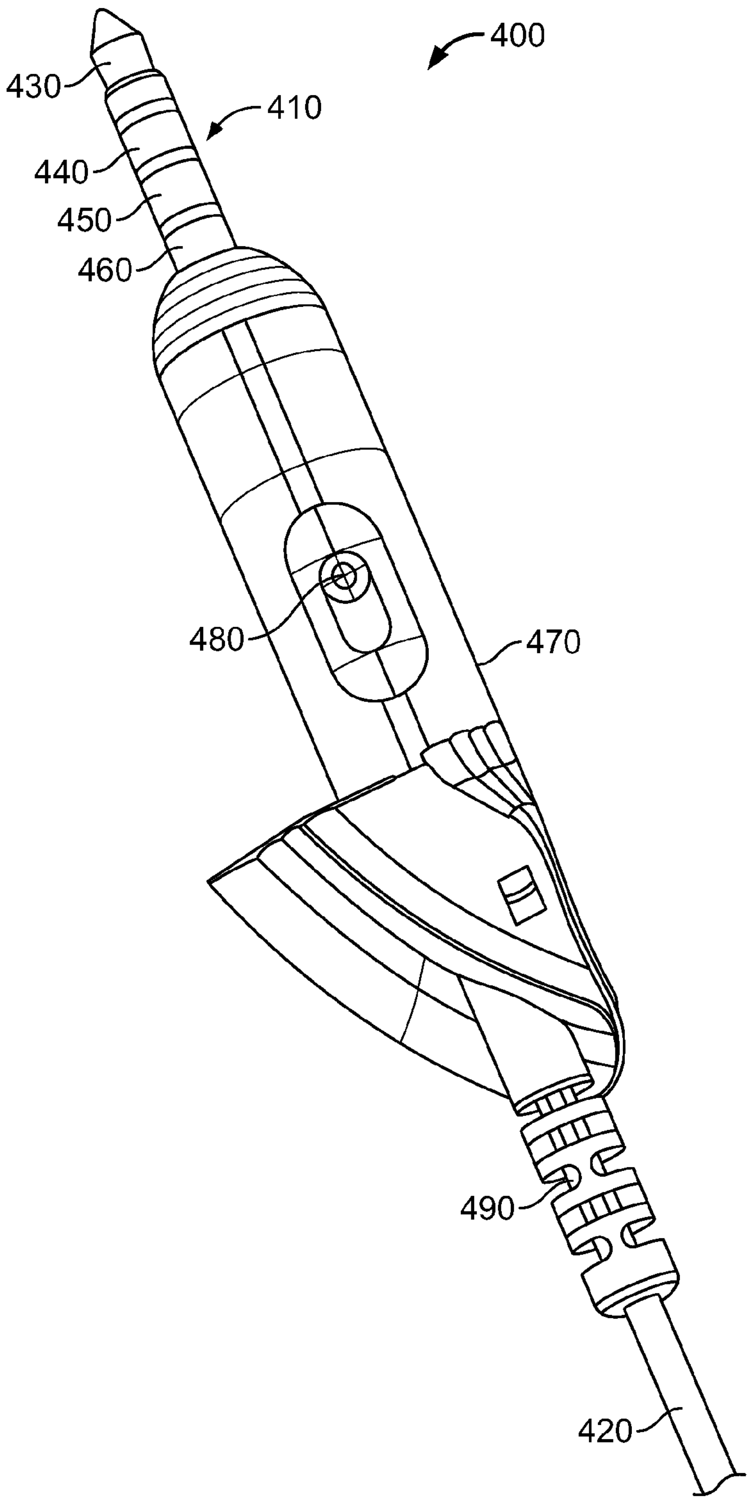
FIG. 5 is a side view of a headphone jack.

Referring to FIG. 5, the body 470 of the accessory plug 410 may contain embedded or in-line electronics to perform various functions, such as audio and voice level control or passive configuration to an accessory. The body 470, as shown, may also contain a switch 480 that may be configured for use as an on/off power switch, an audio attenuation switch, a mute switch, or the like. Alternatively, body 470 may be enlarged as shown in FIG. 2 to house all accessory electronics.

The plug 410 may mate with the jack 154 through the accessory insertion channel 153 in the headphone 100. The accessory plug 410 may contain a strain relief 490 and be coupled to a single, dual, or multiple conductor cable 420 connection to an accessory. The cable 420 and plug 410 may provide the headphone 100 with the physical ability to interface with, for example, an audio output from a stereo or MP3 player, a hands-free connection to a cell phone (wired or wireless), a microphone for voice sensing, an aviation or helicopter, a connection to a USB host, or the like. For this purpose the other end of the cable may be fitted with a plug, a socket, or another kind of connector or be wired directly to the accessory. Or as previously described, the accessory can be attached directly to the plug without the use of any cable.

The plug 410 of the accessory cable 400 comprises four separate contacts that allow the headphone to connect to the accessories. The contacts may, in this example be configured to serve a power circuit 430, a left audio channel 440, a right audio channel 450, and a common or ground circuit 460. In some implementations, the power circuit 430 may be configured as a handshaking, configuration control, or communication interface line (e.g., Va 318, as described above) between the headphone 100 and the accessory. Conductors in the cable are connected respectively to each of the contacts.

In some implementations, one or more of the contacts and cable conductors can be dedicated to and carry only power, one or more others may be dedicated to and carry only audio signals, one or more others may be dedicated to carry only control, management, or command signals, or one or more contacts and cable conductors may carry any combination of power, audio signals, and control/command/management signals by appropriate multiplexing techniques. In some implementations, connectors other than a coaxial multi-contact phone plug may be used to connect the headphone to the accessory. In some implementations, the cable is permanently attached to the head-mounted device, and accessories are connected to the free end of the cable.

Figure 6:
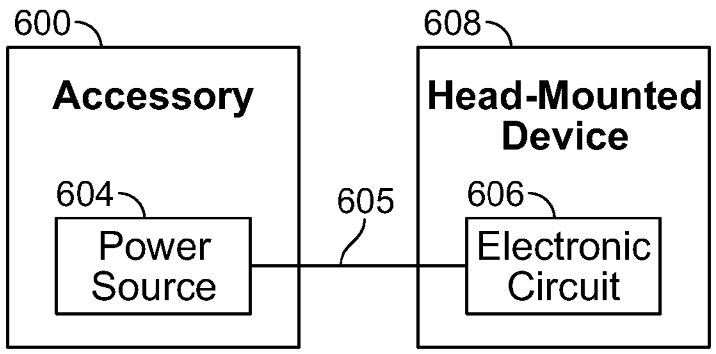
FIG. 6 is a block diagram.

In some implementations, for example, as shown in FIG. 6, an accessory 600 such as a portable music player, radio, cell phone, or other audio communication device may have its own internal power source 604, and the power from that source may be carried by a conductor 605 to power electronic circuits 606 involved in providing audio to a user within a head-mounted device 608, for example, an ANR circuitry, amplification circuitry or other audio processing circuitry in a headphone.

Other embodiments are also within the scope of the following claims.

What is claimed is:

1. A method comprising
- detecting a coupling of a head-mounted device to a separate accessory,
- determining if the separate accessory is compatible with the head-mounted device by communicating a configuration protocol between the head-mounted device and the separate accessory that passes at least one of a binary or integer preset value from the separate accessory to the head-mounted device, and if the separate accessory is determined to be compatible based upon the preset value, delivering power from a power source in the head-mounted device to the separate accessory that is coupled to the head-mounted device,
- passing signals back and forth between the head-mounted device and the accessory, and
- configuring one or both of the head-mounted device and the accessory based on the signals.

2. The method of claim 1 in which the head-mounted device comprises at least one of a headphone and a headset.

3. The method of claim 1 in which the head-mounted device comprises an audio device.

4. The method of claim 1 in which the accessory comprises at least one of a music player, a wireless receiver, a wireless transceiver or a radio.

5. The method of claim 1 in which the device and the accessory are coupled using a detachable cable.

6. The method of claim 1 also comprising delivering power and signals on a common conductor that couples the head-mounted device to the accessory.

7. An apparatus comprising
- an audio device to be mounted on a head of a user and comprising a transducer to deliver sound to an ear and a power source,
- a circuit to determine if a separate accessory adapted to couple to the audio device is compatible with the audio device by communicating a configuration protocol between the audio device and the separate accessory that passes at least one of a binary or integer preset value from the separate accessory to the audio device,
- a conductor to deliver power from the power source to a separate accessory coupled to the audio device if the circuit determines that the separate accessory is compatible with the audio device based upon the preset value,
- a signaling device to communicate with an accessory that is connected to the audio device, and a wired channel to carry configuration signals back and forth between the audio device and the separate accessory.

8. The apparatus of claim 7 in which the head-mounted device comprises at least one of a headphone and a headset.

9. The apparatus of claim 7 in which the head-mounted device comprises an audio device.

10. The apparatus of claim 7 in which the power is delivered from a source of power in the head-mounted device.

11. The apparatus of claim 10 in which the source of power comprises a battery.

12. The apparatus of claim 7 in which the accessory comprises at least one of a music player, a wireless receiver, a wireless transceiver, or a radio.

13. The apparatus of claim 7 in which the device and the accessory are coupled using a detachable cable that includes the conductor.

14. The apparatus of claim 7 in which the conductor is dedicated to delivering power.

15. The apparatus of claim 7 in which the accessory is peripheral to the head-mounted device.

16. The apparatus of claim 7 also including a signaling device to communicate with an accessory that is connected to the audio device, and a common conductor to carry power from the audio device to the separate accessory to carry signals between the audio device and the accessory.

17. The apparatus of claim 7 in which the signals comprise at least one of command, control, or management signals.

18. An apparatus comprising an accessory to be coupled to a head-mounted device, the accessory having a conductor to connect to a power conductor of the device to receive power for the accessory, a circuit to determine if the accessory is compatible with the audio device by communicating a configuration protocol between the head-mounted device and the accessory that passes at least one of a binary or integer preset value from the accessory to the head-mounted device, and if the accessory is compatible with the audio device based upon the preset value, to provide power to the accessory on the conductor, and the accessory comprises a signaling device to conduct wired communication of configuration signals with the head-mounted device.

19. The apparatus of claim 18 in which the head-mounted device comprises at least one of a headphone and a headset.

20. The apparatus of claim 18 in which the head-mounted device comprises an audio device.

21. The apparatus of claim 18 in which power is delivered from a source of power in the head-mounted device to the accessory.

22. The apparatus of claim 21 in which the source of power comprises a battery.

23. The apparatus of claim 18 in which the accessory is peripheral to the head-mounted device.

24. The apparatus of claim 18 in which the accessory comprises at least one of a music player, a wireless receiver, a wireless transceiver, or a radio.

25. The apparatus of claim 18 in which the device and the accessory are coupled using a detachable cable that includes the conductor.

26. The apparatus of claim 18 in which the accessory comprises a common conductor that carries power and signals between the accessory and the head-mounted device.

27. The apparatus of claim 18 in which the accessory comprises a device that uses power and a conductor to receive power for the device from a head-mounted device.

28. A method comprising detecting a coupling of a head-mounted device to a portable accessory, determining if the separate accessory is compatible with the head-mounted device by communicating a configuration protocol between the head-mounted device and the separate accessory that passes at least one of a binary or integer preset value from the separate accessory to the head-mounted device, and if the separate accessory is determined to be compatible based upon the preset value, delivering power from a power source in the portable accessory to the head-mounted device that is coupled to the portable accessory and uses the power for circuitry in the head-mounted device that delivers audio to a user, passing signals back and forth between the accessory and the head-mounted device, and configuring one or both of the accessory and the head-mounted device based on the signal.

29. A method comprising detecting a coupling of a head-mounted device to a separate accessory, determining if the separate accessory is compatible with the head-mounted device when the accessory is coupled to the head mounted device by communicating a configuration protocol between the head-mounted device and the separate accessory that passes at least one of a binary or integer preset value from the separate accessory to the head-mounted device, and if the separate accessory is determined to be compatible based upon the preset value, delivering power from a power source in the head-mounted device to the separate accessory that is coupled to the head-mounted device, wherein the head-mounted device includes active noise reduction circuitry.

30. The apparatus of claim 29 in which the power is from a battery of the head-mounted device.

31. The apparatus of claim 29 in which the accessory is one of wireless transceiver, cell phone or communication device.

32. The method of claim 28 in which the signals comprise an identifier for that accessory.

33. The method of claim 32 in which the identifier is used to determine accessory compatibility.

34. The apparatus of claim 18 in which the signals comprise an identifier for the accessory.

35. The apparatus of claim 34 in which the identifier is used to determine accessory compatibility.

36. The method of claim 1 in which the signals comprise an input impedance setting for the head-mounted device.

37. The method of claim 1 in which the accessory comprises a signaling device to set the head-mounted device input impedance.

38. The apparatus of claim 18 in which the signals comprise an input impedance setting for the head-mounted device.

39. The apparatus of claim 18 in which the signaling device is configured to set the head-mounted device input impedance.

* * * * *